US00PP19067P2

(12) United States Plant Patent
Giesen

(10) Patent No.: US PP19,067 P2
(45) Date of Patent: Aug. 5, 2008

(54) ***LOBELIA* PLANT NAMED 'TECH HELITBULE'**

(50) Latin Name: *Lobelia erinus*
Varietal Denomination: Tech Helitbule

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/732,441

(22) Filed: Apr. 3, 2007

(51) Int. Cl.
*A01H 5/00* (2006.01)

(52) U.S. Cl. ..... Plt./451; Plt./263
(58) Field of Classification Search ..... Plt./451, Plt./263
See application file for complete search history.

*Primary Examiner*—Kent L. Bell
*Assistant Examiner*—S. B. McCormick-Ewoldt
(74) *Attorney, Agent, or Firm*—Jondle & Associates, P.C.

(57) ABSTRACT

A new *Lobelia* plant particularly distinguished by its slightly upright, mounded, and semi-compact form, vigorous plant habit, dense and free branching, short internodes, large, light blue colored flowers and tolerance to heat is disclosed.

1 Drawing Sheet

Genus and species: *Lobelia erinus.*
Variety denomination: 'Tech Helitbule'.

BACKGROUND OF THE NEW PLANT

The present invention comprises a new and distinct cultivar of *lobelia,* botanically known as *Lobelia erinus,* and hereinafter referred to by the cultivar name 'Tech Helitbule'. The new cultivar originated from a hybridization made in January 2002 in Andijk, The Netherlands. The female parent was 'LOB03-114-1', a light blue proprietary *lobelia* line (unpatented), while the male parent was 'LOB02-14-2', a blue proprietary *lobelia* line (unpatented).

The seeds produced by the pollination were sown in March 2003. A single plant selection was chosen for further evaluation and for asexual propagation in July 2003.

The new cultivar was created in 2002 and has been asexually reproduced repeatedly by vegetative cuttings and tissue culture in Gilroy, Calif., and Andijk, The Netherlands over a three and a half year period. The plant has also been trialed at Gilroy, Calif., Andijk, The Netherlands and Hillscheid, Germany. The present invention has been found to retain its distinctive characteristics through successive asexual propagations.

Plant Breeder's Rights for this cultivar have been applied for with the European Union on Nov. 13, 2006.

SUMMARY OF THE INVENTION

The following are the most outstanding and distinguishing characteristics of this new cultivar when grown under normal horticultural practices in Gilroy, Calif., and Andijk, The Netherlands.

1. Slightly upright, mounded, and semi-compact form,
2. Vigorous plant habit,
3. Dense and free branching,
4. Short internodes,
5. Large, light blue colored flowers; and
6. Tolerance to heat.

DESCRIPTION OF PHOTOGRAPHS

This new *lobelia* plant is illustrated by the accompanying photographs which show overall plant habit including blooms, buds, and foliage of the plant in full color of 20 to 23 weeks old plants. The plants were grown in a greenhouse during the late spring months before being moved to an outdoor setting in Andijk, The Netherlands during the summer. The photographs were taken in August 2005. The colors shown are as true as can be reasonably obtained by conventional photographic procedures.

DESCRIPTION OF THE NEW CULTIVAR

Figure 1:
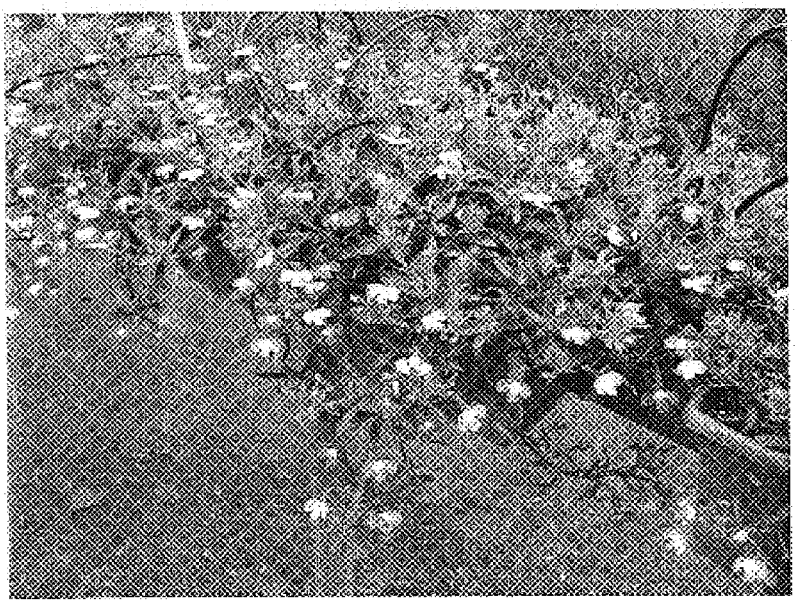
FIG. 1 shows the overall plant habit including blooms, buds, and mature foliage as well as immature and mature flowers.
Figure 2:
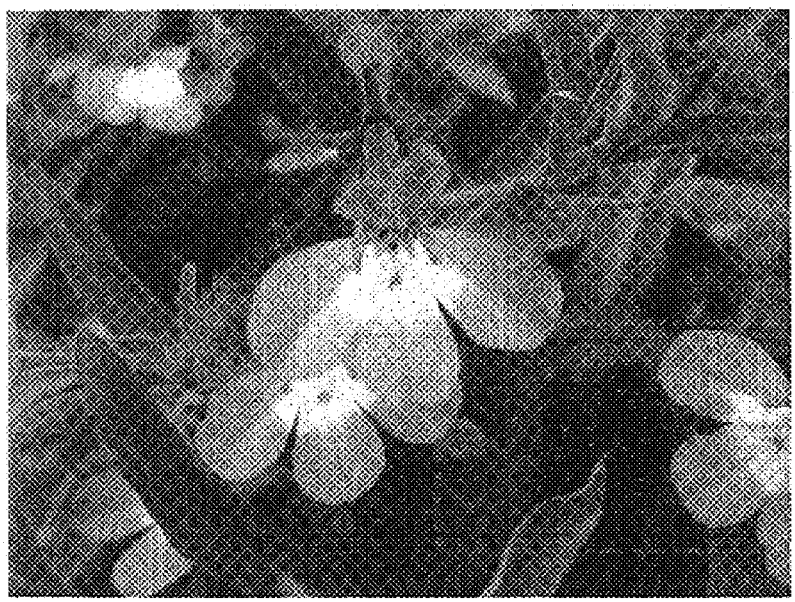
FIG. 2 shows a close-up of an immature flower prior to the deep blue color fading to a lighter blue.

The following detailed descriptions set forth the distinctive characteristics of 'Tech Helitbule'. The data which define these characteristics were collected in the fall and winter season from 20 to 24 weeks old plants grown in 6-inch pots in Gilroy, Calif. The plants had one plant growth regulator treatment and one terminal pinch at the onset of the trial. Color readings were taken in a LEXAN-covered greenhouse in January 2007 under natural light. Color references are primarily to the R.H.S. Colour Chart of The Royal Horticultural Society of London (R.H.S.) (2001 edition). Texture description details were observed under a dissecting microscope.

DETAILED BOTANICAL DESCRIPTION

Classification:
*Botanical.—Lobelia erinus.*
*Common name.—Lobelia.*
Parentage:
*Female parent.*—'LOB03-114-1' proprietary *lobelia* line (unpatented).
*Male parent.*—'LOB02-14-2' proprietary *lobelia* line (unpatented).

Growth:

*Growth and branching habit.*—Good vigorous habit, dense and freely branched with short internodes; exhibits some heat tolerance.

*Form.*—Herbaceous annual; slightly upright but mounding, pendulous and semi-compact.

*Height (measured from the top of the soil, including any flowers).*—20.0 cm to 25.0 cm.

*Width (horizontal plant diameter, including any flowers).*—60.0 cm to 65.0 cm.

*Time to produce a finished flowering plant.*—9 to 10 weeks for a 6-inch pot.

*Outdoor plant performance.*—Patio planters in mixed container plantings or garden beds.

*Time to initiate roots.*—21 to 28 days at 68 to 74 degrees Fahrenheit.

*Root description.*—Fibrous, freely-branching, and white.

Leaves:

*Arrangement.*—Alternate.

*Color.*—Immature leaf: Upper surface: Closest to RHS 138A. Lower surface: Closest to RHS 137D. Mature leaf: Upper surface: Closest to RHS 137A. Lower surface: Closest to RHS 137D.

*Length.*—4.5 cm to 4.8 cm.

*Width.*—2.0 cm to 2.6 cm.

*Shape.*—Oblanceolate to obovate.

*Margin.*—Crenate; slightly toothed.

*Apex.*—Retuse.

*Base.*—Cuneate.

*Texture.*—Pilose.

*Venation.*—Pinnate.

*Venation color.*—RHS 144C.

Stems:

*Length.*—4.0 cm to 4.6 cm.

*Diameter.*—0.3 cm.

*Internode length.*—2.5 cm to 3.0 cm.

*Color.*—RHS 137A.

*Texture.*—Pilose.

*Stem anthocyanin.*—Absent.

*Peduncle.*—Color: RHS 137B. Length: 2.3 cm to 3.7 cm. Diameter: 0.1 cm. Texture: Pilose.

Flower buds:

*Shape.*—Oval to oblong.

*Diameter.*—0.4 cm to 0.5 cm.

*Length.*—0.9 cm to 1.4 cm.

*Color when bud is first starting to open.*—RHS 1C but a little greyer with slight shading of RHS N187C starting to show.

Inflorescence:

*Blooming habit.*—Plants flower freely and continuously in the growing season from spring to the fall.

*Lastingness of individual blooms on plant.*—5 to 8 days depending on environmental conditions.

*Fragrance.*—None.

*Inflorescence type.*—Flowers form at apical axils, with one flower per axil; flowers are labiate; upper petal has two small lobes and lower lip has three larger and broader lobes; lobes are fused at the base.

*Quantity of flowers and buds per flowering branch.*—20 to 25.

Flowers:

*Flower diameter (horizontal).*—1.9 cm to 2.2 cm.

*Flower height (vertical).*—1.5 cm to 1.7 cm.

*Immature flower.*—Color: Both upper and lower surfaces: Upper surface: Closest to RHS 100B; lower surface: RHS 97D.

*Mature flower.*—Upper lobe: Color: Upper surface: Closest to RHS 97A, fading to RHS 97B. Lower surface: RHS 97D. Length: 0.7 cm to 0.8 cm. Width: 0.3 cm. Shape: Oblanceolate. Apex: Abruptly acute. Margin: Entire. Texture: Papillose. Lower lobes: Color: Upper surface: A little lighter than RHS 97A, fading to RHS 97B; basal 'eye' of RHS N155D but whiter; few basal spots of RHS 97A inside the white 'eye'. Lower surface: RHS 97D. Length: 1.0 cm to 1.2 cm. Width: 0.7 cm to 1.2 cm. Shape: Obovate. Apex: Mucronulate. Margin: Entire. Texture: Papillose.

*Corolla.*—Color: Inside: RHS 97D; small spots of RHS N88C; two basal bars of RHS 144B. Outside: RHS 97D. Tube length: 1.0 cm. Diameter: 0.5 cm at the throat; 0.2 cm to 0.25 at the base.

*Calyx.*—Five sepals with fused bases that curve out and away from the corolla. Color, both surfaces: RHS 137A. Length: 0.7 cm to 0.8 cm. Diameter: 0.2 cm at the widest point. Shape: Linear to lanceolate. Apex: Acuminate. Texture: Pilose.

Reproductive organs:

*Androecium.*—Number of anthers: 5 fused around the stigma. Filament length: 0.7 cm. Filament color: RHS N155B but whiter. Pollen color: RHS 4C. Pollen amount: Moderate.

*Gynoecium.*—Pistil length: 1.1 cm. Stigma color: RHS N82C. Style color: RHS 145A. Style length: 0.7 cm to 0.8 cm.

Fruit and seed set: Has not been observed.

Disease and insect resistance: Resistance and susceptibility is typical of the species.

COMPARISON WITH KNOWN CULTIVARS

'Tech Helitbule' differs from the female parent, 'LOB03-114-1', proprietary breeding line (unpatented), in that 'Tech Helitbule' has longer stems than 'LOB03-114-1'. Additionally, 'Tech Helitbule' has larger and darker blue flowers and has a more vigorous plant habit than 'LOB03-114-1'.

'Tech Helitbule' differs from the male parent, 'LOB02-14-2', proprietary breeding line (unpatented), in that 'Tech Helitbule' has a little smaller plant habit. Additionally, 'Tech Helitbule' has longer and thicker stems along with larger and lighter blue flowers than 'LOB02-14-2'.

'Tech Helitbule' differs from the commercial variety 'Balobwablu' (U.S. Plant Pat. No. 16,524) in that 'Tech Helitbule' has a larger plant habit with longer stems than 'Balobwablu'. Additionally, 'Tech Helitbule' has a longer pedicel with a lighter flower color than 'Balobwablu'.

I claim:

1. A new and distinct *Lobelia* plant as shown and described herein.

* * * * *